United States Patent [19]

Grayzel

[11] Patent Number: 4,936,022
[45] Date of Patent: Jun. 26, 1990

[54] MULTI-LEG CALIPER WITH HEART SCALE

[76] Inventor: Joseph Grayzel, 262 Fountain Rd., Englewood, N.J. 07631

[21] Appl. No.: 135,668

[22] Filed: Dec. 21, 1987

[51] Int. Cl.⁵ .................................................. G01B 3/16
[52] U.S. Cl. ...................................... 33/664; 33/558.02; 33/558.03; 33/558.2; 33/1 C
[58] Field of Search ...................... 33/1 B, 1 C, 149 B, 33/150, 151, 663, 664, 665, 558.01, 558.02, 558.03, 558.2; 128/702, 706, 710

[56] References Cited

U.S. PATENT DOCUMENTS

| | | | |
|---|---|---|---|
| 425,168 | 4/1890 | Gale | 33/664 |
| 495,219 | 4/1893 | Goldschmitt | 33/664 |
| 1,258,574 | 3/1918 | Jones | 33/664 |
| 1,624,031 | 4/1927 | Adler | 33/664 |
| 1,643,968 | 10/1927 | Thompson | 33/664 |
| 4,550,502 | 11/1985 | Grayzel | 33/1 C |

FOREIGN PATENT DOCUMENTS 174215  3/1953  Austria .................... 33/150

Primary Examiner—William A. Cuchlinski, Jr.
Assistant Examiner—Patrick R. Scanlon
Attorney, Agent, or Firm—Weingram & Zall

[57] ABSTRACT

A multi-leg caliper with heart scale allowing analysis over a variable plurality of heart beats for arrhythmia is taught. Briefly stated, a plurality of parallel members are pivotally connected to a second set of parallel members thereby forming a lattice structure. Points are disposed at one end of each of the first mentioned parallel members which are placed against certain events recorded on an ECG strip chart. Pivot points associated with the opposite ends of the pointed parallel members are placed against a scale which is suitably calibrated to indicate various heart beat criteria. Also disclosed is a method of analyzing information and characteristics contained on an electrocardiogram chart by placing an indicia chart adjacent a multi-leg caliper, placing the multi-leg caliper adjacent prominent events recorded on an electrocardiogram chart and comparing values on the indicia chart adjacent indicating portions on the multi-leg caliper, thereby determining the characteristics of the electrocardiogram chart.

4 Claims, 3 Drawing Sheets

MULTI-LEG CALIPER WITH HEART SCALE

BACKGROUND OF THE INVENTION

1. Field of the Invention

The present invention relates to medical instruments and specifically to a mechanical caliper which is intended for use in conjunction with a heart scale in order to analyze recorded electrocardiograms as disclosed in my U.S. Pat. No. 4,550,502, issued Nov. 5, 1985.

2. Description of the Prior Art

An electrocardiograph is an instrument to be applied to the human body for the purpose of making a graph, or recorded line, for indicating the operations of the heart, such as the expansion and contraction of the heart muscle, which is accompanied by electric currents. The electrocardiograph records the changes of electrical potential occurring in the form of a tracing on a paper chart or strip divided into 1.0 mm square blocks which are representative of units of time (25 mm=1.0 sec. or 1.0 mm=0.040 sec.).

The normal heart rate of an adult is considered to lie between 60 and 100 beats per minute. Slower rates often enable the emergence of extra, irregular beats in a transition to a very rapid heart rate. Fast heart rates, often described as palpitations of the heart, may follow irregular beating and produce weakness, fatigue, anxiety and faintness. The ultimate danger from all types of alterations in the rhythm of the heartbeat of cardiac arrhythmias is the progression of cardiac arrest and sudden death.

A great variety and number of cardiac rhythmic disturbances and disease rhythm mechanisms point up the magnitude of the diagnostic problem facing a physician who must make a definitive diagnosis before selecting a medication to treat the arrhythmia. Also, with the variety of anti-arrhythmic medications available, each possessing its own mode of action and nuance of effect, precise diagnosis of the arrhythmia is most important for selection of optimum therapy.

In view of the magnitude of the problems of accurate diagnosis and matching of medication to the arrhythmia, the need for a diagnostic tool for the study of arrhythmias as recorded on the conventional cardiographic chart or strip is apparent.

Various time intervals on the electrocardiograph (ECG) waveform are of importance, such as heart rate, cycle duration, time of onset of the P-wave to onset of the QRS-wave (PR interval), and the time from the onset of the QRS-wave to the end of the T-wave (QT interval). In order to evaluate these intervals for abnormalities, several measurements and corrections are required which are made by calculations or through the use of reference tables.

Diagnosis of the rhythm requires analysis of the regularity or irregularity of the rhythm, the nature of the irregularities, variation of intervals between beats and comparison of successive intervals, variation of intervals among a series of sequence of beats, separate, respective beating of upper chambers (atria) and lower chambers (ventricles), and the relation between the beating of the atria and the beating of the ventricles.

An instrument is obviously required which enables rapid, accurate measurement of successive intervals between beats and also provides a means for comparison of such intervals.

It is desirable that any such instrument provides the capabilities for simultaneous assessment of a group or series of beats and intervals.

My U.S. Pat. No. 4,550,502 discloses and claims a gauge which facilitates the analysis of a group or sequence of heartbeats recorded on a cardiographic chart in order to diagnose the cardiac rhythm. The guage comprises a flat sheet of transparent material having a plurality, or fan, of straight diverging lines disposed on the sheet; and a plurality of straight parallel lines disposed on the sheet extending in a direction transverse to said diverging lines and perpendicular to a line extending medially between the outermost of said diverging lines. The diverging lines are angularly spaced with respect to one another so as to intercept equal increments along each particular horizontal line. The transverse lines are spacially arranged such that they interact with the diverging lines to form a grid. The distance between adjacent points of intersection with the diverging lines and any of the parallel lines bears a relation to the heartbeat rate or heart cycle interval of a periodic waveform recorded on a cardiographic chart. Indicia are disposed on the sheet for designating the transverse parallel lines as graduations of a scale comprising intervals which correspond to heartbeat cycle intervals or heartbeat rate. The gauge is physically sized so that outermost of the diverging lines are laterally spaced apart to encompass at least six heartbeat cycles of the periodic waveform.

As discussed in that patent, a caliper is described as being utilized to compare successive heart beat cycles. Such a caliper is characterized as an instrument which is adjusted to the interval of a single heartbeat. A limitation on this divider approach however is that such a device is limited in use to examining one beat at a time and then comparing one beat to the next. The dividers of the prior art do not provide for simultanous analysis of a group or sequence of beats so that the rhythm created by the sequence of beats could be observed and any departure from irregularity would be immediately revealed.

The multi-leg caliper of the present invention solves the problems characterized above and described in my U.S. Pat. No. 4,550,502.

The use of various dividers predates my U.S. Pat. No. 4,550,502. Such use may be found in Italian Patent No. 445,972, dated Mar. 4, 1949, and German Patent No. 269,832, dated Nov. 16, 1950. However, both of these dividers do not allow comparison between multiple points and a chart of any kind directly adjacent thereto.

A number of other divider devices are known, which have members that move about a central pivot point in a fan like shape. Examples of this may be found in French Patent No. 437,458, dated Apr. 22, 1912; U.S. Pat. No. 495,219, dated Apr. 11, 1893; U.S. Pat. No. 3,271,869, dated Sept. 13, 1966; and German Patent No. 240,481, dated Apr. 16, 1946. These all have the distinct disadvantage that all points must move with respect to an upper central pivot point thereby making attachment to a removable scale difficult while precluding compactness in the extended or closed state. Further, many do not allow for movement of the points along a straight line but rather move in an arcuate fashion.

Another type of divider may be found in U.S. Pat. No. 235,225, dated Dec. 7, 1880. While all pivot points in this type of device remain along a straight line during expansion or contraction, unlike the fanlike structure in the previously described patents, this instrument is expressly used for mechanical drafting purposes only. U.S. Pat. No. 774,718, issued Nov. 8, 1904, relates to a ruling machine having pens and pen holders movably supported so as to be adjustable toward and away from each. The pens are used to rule lines on a paper at varying distances apart. Therefore the divider is not actually used for measurement but for producing parallel lines. U.S. Pat. No. 791,235, issued May 30, 1905, is intended for drafting use in the layout of ductwork, plumbing and the like, and as such is exclusively used for dividing a distance into equal parts and not for comparison with scales, charts or the like. British Patent No. 1219, dated Jul. 17, 1913, is similar in concept and use to previously mentioned Pat. No. 791,235 and is used merely for dividing distances up for use by carpenters, drawing purposes and the like. U.S. Pat. No. 1,643,968, issued Oct. 4, 1927, is used for making optional adjustments in a spaced relation between markers and is again used exclusively for dividing a distance up into a plurality of equidistant spaces. U.S. Pat. No. 1,696,832, issued Dec. 25, 1928, is also used for dividing a distance into a number of equidistant arranged spaces in a single operation. However, none of the above-mentioned patents utilizes the concept of using calipers or dividers for comparison of one distance with respect to another along the same line while simultaneously allowing for direct comparison to a medically related rhythm rule or the like.

SUMMARY OF THE INVENTION

A multi-leg caliper with heart scale allowing analysis over a variable plurality of heart beats for arrhythmia is taught. Briefly stated, a plurality of parallel members are pivotally connected to a second set of parallel members thereby forming a lattice structure. Points are disposed at one end of each of the first mentioned parallel members which are placed against certain events recorded on an ECG strip chart. Pivot points associated with the opposite ends of the pointed parallel members are placed against a scale which is suitably calibrated to indicate various heart beat criteria. Also disclosed is a method of analyzing information and characteristics contained on a cardiographic chart by placing an indicia chart adjacent a multi-leg caliper, placing the multi-leg caliper adjacent prominent events recorded on a cardiographic chart and comparing values on the indicia chart adjacent indicating portions on the multi-leg caliper, thereby determining the characteristics of the cardiographic chart.

Accordingly, a principal object of the present invention is to provide a device and method which can analyze a group of beats simultaneously. Another object of the present invention is to provide a means to measure the interval between beats. It is an object of the present invention to provide a means for measuring the interval between specific events which occur during the beat for comparison with successive similar occurrences in successive beats. A further object of the present invention is to provide a device which can compare the values of successive intervals. It is an object of the present invention to provide an aid to prediction or searching for the occurrence of irregular beats appearing on a chart.

An important object of the present invention is to locate or define points precisely on an ECG chart. A still further object of the present invention is to precisely define points and intervals with an error less than 4 msec (which corresponds to 0.1 mm on a graphic ECG chart recorded at a standard speed of 25 mm/sec, 0.04 sec/mm or 40 millisec/mm).

Another object of the present invention is to provide a device which can continuously vary the length or intervals in the device so that precise matching of any rate or period can be accomplished. A still further object of the present invention is to provide a device which accomplishes all of the foregoing objects while still being maintained as a compact, geometric instrument.

It is yet another object of the present invention to provide an apparatus for analyzing cardiographic charts which can be conveniently carried by the user. A further object of the present invention is to provide a device which includes a cover means to protect the user from exposure to the points on the device.

In addition to the foregoing objects and advantages, other advantages and purposes will become apparent to those skilled in the art from a review of the detailed specification of my invention which follows.

DESCRIPTION OF THE DRAWINGS

Reference in the specification is made to the accompanying drawings in which.

DESCRIPTION OF THE PREFERRED EMBODIMENT

Construction of the Present Invention

Figure 1:
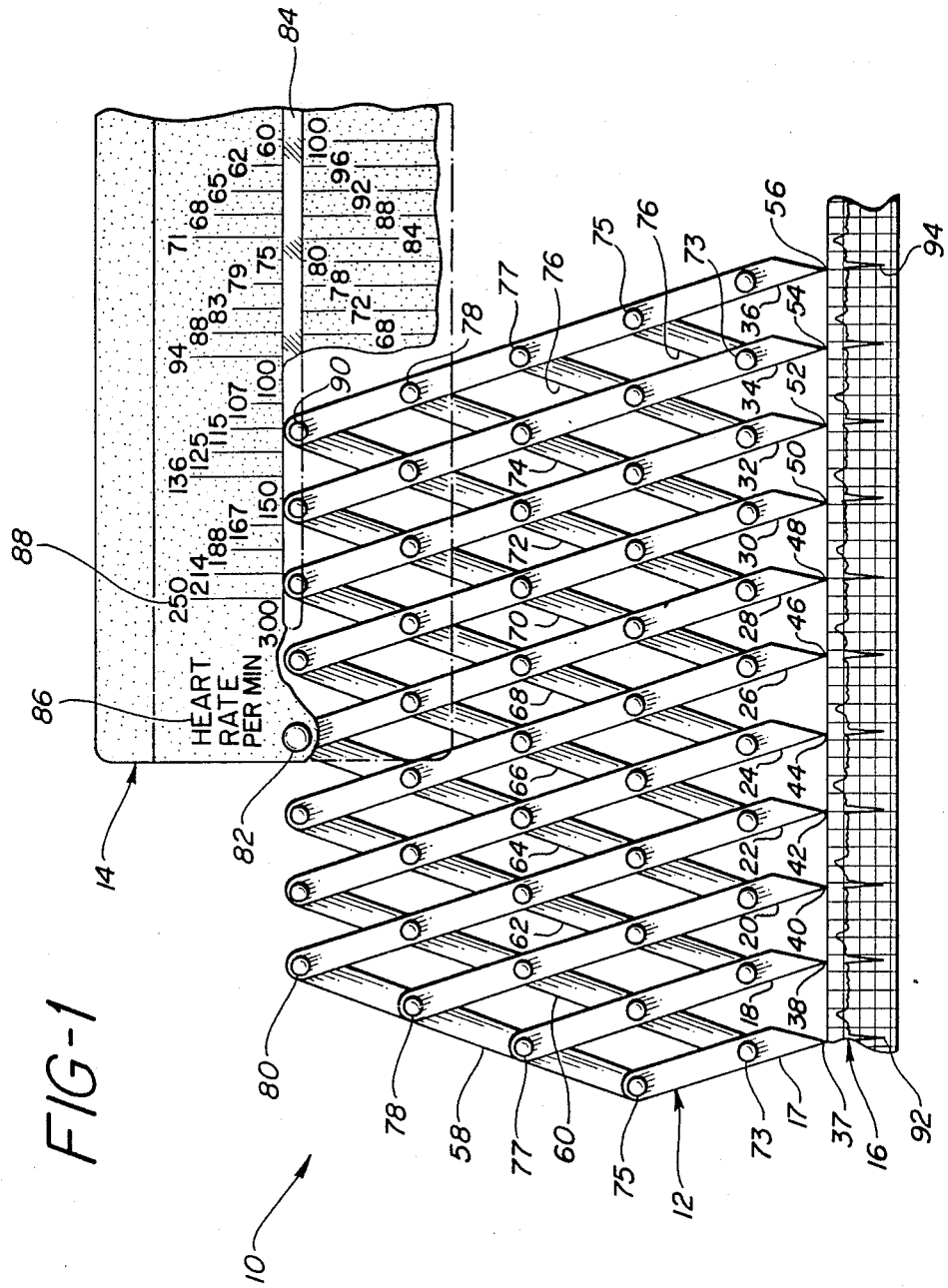
FIG. 1 is a plan view of the device in accordance with my invention.

Referring now to FIG. 1, there is shown the multi-leg caliper with heart scale, shown generally at 10, adjacent to a cardiographic (ECG) chart 16. More particularly, a multi-leg caliper is shown generally at 12 and is attached to a heart scale shown generally at 14. The multi-leg caliper 12 is comprised of eleven parallel members hereinafter designated as the first parallel member 17, second parallel member 18 through the eleventh parallel member 36. Disposed at the end of each parallel member is a point such that first parallel member 17 has disposed at its end a first point 37, while similarly second parallel member through eleventh parallel member have second through eleventh points 38-56 respectively disposed thereat. Eleven cross members are disposed parallel to each other and at an angle with respect to the first through eleventh parallel members 17-36 and are hereafter designated as first cross member 58, and second cross member 60 through eleventh cross member 76. At each crossing of a parallel member 17-36 with a cross member 58-76, the respective parallel and cross members are pivotally attached to each other by the use of eyelets, rivets, screws, or any other suitable device. This therefore forms a plurality of rows of pivots hereinafter designated as the first or lower pivot row 73, second pivot row 71, third pivot row 77, fourth pivot row 78, and fifth or upper pivot row 80. Although the present invention has eleven points 37-56, a greater or lesser amount may be used.

Accordingly, the multi-leg caliper 12 forms a lattice type of structure wherein the distance between respective points 37-56 may be compressed or expanded merely by pulling on or compressing any two of the pivot rows or by pulling apart or compressing any two parallel members 17-36 or cross members 57-76, or of the points themselves 37-56. Therefore, ten equidistant spaces are delineated between adjacent points 37-56 whenever the multi-leg divider 12 is compressed or expanded.

As shown in FIG. 1, there are eleven parallel members and eleven cross members with five rows of pivots which insure sufficient integrity to the lattice so that movement of any two members of the lattice will proportionately change the entire lattice. Therefore, there is no need for external bracing or separate enlarged end members or super-sized members which are longer than the standard parallel members 22-36 or the standard length cross members 60-72.

The multi-leg caliper is attached or placed adjacent to a heart or rhythm scale 14 at the origin or initial reference point 82, which is disposed at one end of scale 14. Scale 14 is in partial phantom b dashed lines in order to show how it is overlaid onto multi-leg caliper 12. Preferably, the scale 14 is not transparent to light with the exception of area 84 which is transparent and therefore acts as a viewing area enabling viewing of the movement of indicator point 90. All of the pivot points in upper pivot row 80 are made to move parallel to slot-like viewing area 84. This allows sliding reference or indicator point 90 to move within the boundary of viewing area 84 with respect to the heart rate scale 88 contained on the heart rate indicia 86.

Accordingly, by the mentioned expansion and contraction of the multi-leg caliper 12, indicator point 90 will be disposed adjacent to different points on heart rate scale 88 thereby indicating a specified heart rate per minute.

The multi-leg caliper 12 in use is placed adjacent to an ECG chart 16 indicating the regularity and sequence of eleven heart beats over 10 complete cycles. Since the distance between points 37-56 are equidistant, any deviation or irregularity between the onset of a heart beat at 52 and the beginning of the eleventh heart beat 94 may be readily seen. This also allows for the sliding indicator point 90 to be positioned against the corresponding portion of the heart rate scale 88 on the heart rate indicia 86.

Figure 2:
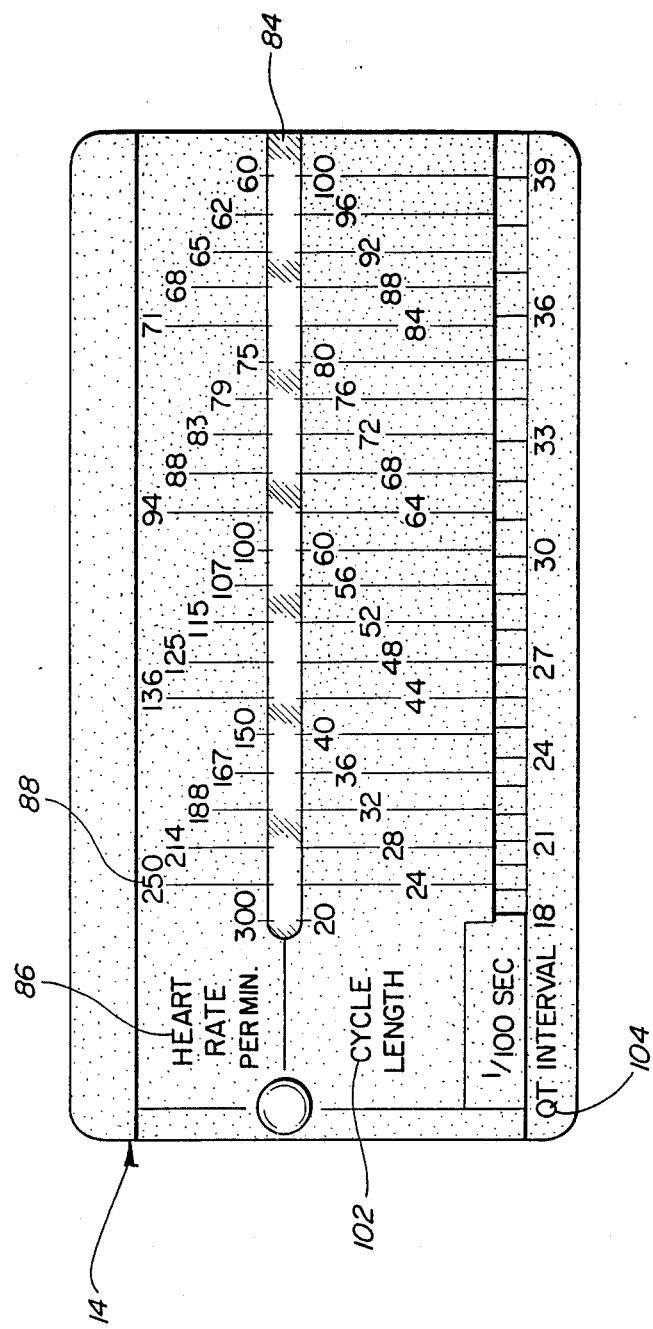
FIG. 2 shows an indicia chart for use with the present invention.

Turning now to FIG. 2, there is shown a complete heart rate scale 14 of that shown in FIg. 1 but having a cycle length indicia and a QT indicia thereon. The heart scale 14 as mentioned is preferably not transparent, with the exception of viewing area 84, having indicia inked or otherwise appropriately placed thereon. The scale is fastened tot he face plane of the multi-leg caliper 12 by means of a rivet extending through one of the pivot points at the intersection of a parallel member and a cross member.

Figure 3A:
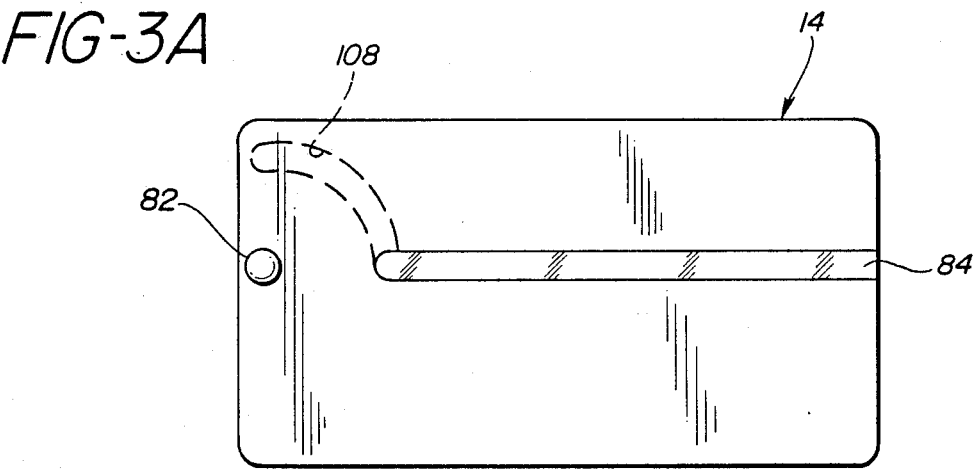
FIGS. 3A and 3B are diagrammatic front and side views, respectively, showing attachment of an indicia chart to the present invention.
Figure 3B:
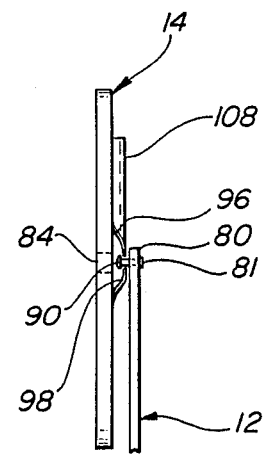

Referring now to FIGS. 3A and 3B, there is shown one means of attachment of the multi-leg caliper 12 to the heart scale 14. Disposed on the rear of the scale 14 and directly behind viewing area 84 are brackets or ledges 96 thereby forming a track 98. The track 98 allows rivets 81 disposed along the upper pivot row 80 to slide therein. Therefore, this will insure that the heart scale 14 remains properly oriented with respect to caliper 12, i.e., horizontal. It is to be understood, however, that track 98 may be formed by separate brackets attached to scale 14 or as part of the molded scale 14. However, it is not a requirement that any sort of horizontal positioning means be provided since the user can manually orient the heart scale to a horizontal position such that the index point 90 can be seen through the transparent slit 84 when a reading is desired. Evident is a secondary or captive track 108 which may be incorporated when caliper 12 is folded or compressed and the heart scale 14 is rotated so as to be vertical and therefore parallel to the caliper 12. Also evident is that, without use of a secondary or captive track 108, scale 14 when rotated 90° clockwise so as to be parallel to compressed caliper 12 is at least coextensive with the lattice structure. In this manner, scale 14 acts as a cover for caliper 12 thereby facilitating placement of the entire device into a pouch or pocket and, during insertion of the device into such pouch or pocket, the lower edge of the cover acts as a protective means to prevent contact of the points with the pouch or pocket.

Figure 4:
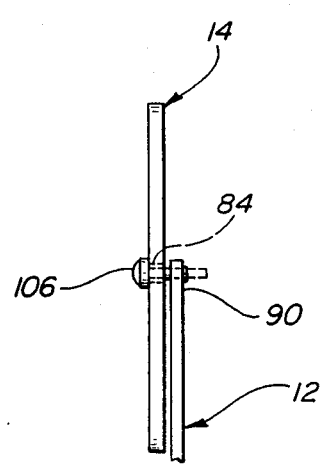
FIG. 4 shows an alternate mode of attachment of an indicia chart to the present invention.

Referring now to FIG. 4, an alternative embodiment showing attachment of the multi-leg caliper 12 to the heart scale 14 is shown. In this, viewing area 84 is a slot in scale 14. Sliding indicator point 90, disposed adjacent viewing area 84, has a knob 106 attached thereto on opposing sides of heart scale 14. When viewing FIG. 4, it is evident that heart scale 14 is disposed on the face of multi-leg caliper 12. However, it is envisioned a knob or hub (shown in dashed lines) may be disposed directly opposite sliding knob 106. Therefore the hub will slide in area 84 and allow sliding indicator point 90 to be guided by area 84. This would allow the operator to move knob 106 back and forth in order to contract or expand the multi-leg caliper 12 in relation to ECG 16.

It has been found that the use of eleven parallel members and cross members which provides ten intervals is effective for comparing an appropriate number of events on a cardiographic chart. Further, it is obvious that accuracy in comparing events on a cardiographic chart is extremely important when minute deviations are to be observed and compared.

For a given number of parallel legs, the minimum number of rows of pivots necessary to provide the maximum uniformity or identity of spacing has been empirically determined. Two equations have been developed which set forth this relationship. The two equations are as follows:

(2) $L = 4(n-2) - 1$ for $L < 11$
(2) $L = 3(n-1) - 1$ for $L > 11$ where L=number of parallel legs or points, and n=number of horizontal rows of pins or pivots connecting the parallel legs with the cross members.

In both equations it is possible to obtain accuracies of spacing and comparisons from point to point of one part per thousand. However, it has been found that for the number of parallel legs being eleven or less, equation number one will provide accuracies of one part in 2,500 and for eleven legs to 23 legs, equation number two will provide accuracies of one part in 2,500. The accuracy of the comparison of points was made by tests using eyelets with normal machine tolerances and normal machining procedures.

Therefore, the expansion or contraction of the caliper 12 allows for even distances between points 37-56. Accordingly, the present device allows for analysis of deviations as low as 2 milliseconds per cycle.

Operation of the Present Invention

The operation or use of the multi-leg caliper with heart scale will be described as a series of steps using the various possible scaling factors and scales that are available to assist in the analysis of an ECG waveform. As will be obvious, many of the steps may be accomplished in any order or may be used independently from other steps to evaluate specific problems or making independent analysis.

In FIG. 1, the first point 37 is placed at the beginning of the onset of the QRS complex or other prominent point on ECG chart. The eleventh point 56 is then placed adjacent the beginning of the eleventh QRS complex on ECG chart 16. By then referring to the sliding indicator point 90, and its position on heart rate scale 88, it can be readily determined that for the ECG 16 shown, a heart rate of 115 beats per minute is present. Similarly, should the user decide to determine the cycle length, cycle length indicia 102 shown in FIG. 2 would indicate a cycle length of 52/100ths of a second for this heart rate and simultaneously indicate a normal QT interval of 28 for that heart rate and cycle length.

Resolution may be made finer by increasing the length of the heart rate indicia 86. As presently shown in FIG. 1, the origin point is positioned at pivot 92 and measures four heart beats and is terminated by sliding reference point 90. The particular four intervals could, of course, be altered by moving the origin point from leg 26 back to leg 24 and the pivot point 90 from leg 36 to leg 34. Moreover, if greater accuracy is desired, additional intervals can be included by increasing the number of parallel legs between the origin or pivot point and the sliding point to add additional intervals. The heart rate indicia would have to be adjusted accordingly. For example, if one additional leg or intval were included, the resolution would be increased by 25%. If two additional intervals were included, the resolution would be increased by 50%. Therefore, once the indicia 86 is enlarged by making it longer, it is readily apparent that a different sliding point reference 90 must be utilized, the specific one depending upon the extent of enlargement.

Also apparent is that variations between any two beats may be also examined. Further, it is readily possible to increase or decrease the number of heart beats or events examined without the necessity to change the scale. Fore example, if only five beats are available for analysis, then the first point 37 would be placed adjacent the onset of ARS complex 92 or any other similar prominent point as described, while the fifth point 44 would be placed adjacent the onset of the fifth QRS complex. Sliding reference point 90 would then be utilized as described. Similarly, if eleventh point 56 were placed adjacent the sixth onset of a QRS complex thereby encompassing five cycles, then sliding indicator point 90 would read exactly twice the actual occurrence rate of the indicia utilized and, for example, using scale 88 of FIG. 1, would indicate a heart rate of 230. This would then be divided in half since ten intervals on the lattice were matched to five cardiac cycles (ten divided by five equals two, which is then divided into the scale utilized).

It is to be understood that many variations of the present invention may be practised without departing from the spirit and scope of the present invention. For example, the number of points may be increased or decreased as desired while the types of indicia may also be changed. Further, the multi-leg caliper itself may be comprised of a number of materials such as plastic, metal, wood or the like while the indicia may also be comprised of clear plastic, paper, wood or the like Further, the present invention makes possible the analysis of other types of cardiographic events such as pacemaker pulses, periodocity, noise, T-wave and the like.

Accordingly, the present invention produces a compact, inexpensive caliper with heart scale which is extremely easy to manufacture, extremely accurate and provides the ability to rapidly detect and analyze arrhythmia in an ECG waveform.

It will be understood that various changes in the details, materials, arrangements or parts and operating conditions which have been herein described and illustrated in order to explain the nature of the invention may be made by those skilled in the art within the principles and scope of the invention as set forth in the appended claims.

I claim:

1. Apparatus for analyzing a cardiographic chart comprising:
    a multi-leg caliper comprising:
        a plurality of equally spaced parallel first members, each having a pointd end and an indicating portion;
        a plurality of parallel cross-members, said cross-members being pivotally coupled to corresponding parallel first members thereby forming a lattice structure which may be varied in size while said pointed ends are maintained collinear throughout said variation in size and said indicating portions are maintained in a mathematical relation to the spacing between said pointed ends: and
    a heart scale connected to said multi-leg caliper, said heart scale comprising:
    indicia means adjacent to at least two of said indicating portions of said multi-leg caliper;
    said indicia means disposed to coact with said indicating portions of said multi-leg caliper such that the position of said pointed ends of said multi-leg caliper adjacent a cardiographic chart causes at least two of said indicating portions to be positioned with respect to said indicia means thereby indicating the desired information and characteristics of said cardiographic chart on said heart scale;
    an elongate transparent viewing area on said heart scale so that at least one of said indicating portions is viewable;
    said heart scale connected to at least one of said indicating portions by a pivotal coupling so as to be pivotally disposable between a first position substantially parallel to said lattice structure when said lattice structure is in a compressed state, and a second position wherein said heart scale is substantially perpendicular to said first position.

2. A device according to claim 1, wherein said pivotal coupling is comprised of a fastening means, and further comprising an elongate track adjacent said elongate transparent viewing area so that at least one fastening means is slidably disposed along said track and further including means for assisting in reentry of said indicating portion along said elongate track when said scale is rotated from said first position into said second position.

3. Apparatus for analyzing a cardiographic chart comprising:
    a multi-leg caliper comprising:
        at least five equally spaced parallel first members, each having a pointed end and an indicating portion opposite said pointed end;
        at least five parallel cross-members;

means pivotally coupling said cross-members to corresponding first members thereby forming a lattice structure which can be expanded and contracted while maintaining said pointed ends of said parallel first members collinear;

said means pivotally coupling said cross-members to corresponding first members comprise a plurality of fastening means;

said indicating portions of said parallel first members maintained in a second collinear relationship and parallel to said pointed ends of said parallel first members; and a heart scale connected to said multi-leg caliper, said heart scale comprising:

indicia means adjacent to said indicating portions, said indicia means having values thereon corresponding to information and characteristics of a cardiographic chart;

said indicia means further having an elongate viewing area therein;

a reference point disposed on said indicia means so that disposing said reference point of said indicia means and another indicating portion of said caliper to be visible in said viewing area, and positioning at least two of said pointed ends adjacent said cardiographic chart will place said another indicating portion adjacent said values on said indicia means, thereby indicating the desired information and characteristics of a cardiographic chart;

said heart scale further comprising:

an elongate track adjacent said elongate viewing area to have at least one of said fastening means slidably disposed in said track; and means for assisting in reentry of said indicating portion into said elongate track when said scale is rotated from a first position to a second position.

4. A device according to claim 3, further comprising an elongate track adjacent said elongate viewing area wherein at least one of said indicating portions is slidably disposed in said track and wherein a captive means is used to assist reentry of said at least one of said indicating portions into said elongate track when said scale is rotated from a first position to a second position.

* * * * *